US008642356B2

(12) United States Patent
Chung et al.

(10) Patent No.: US 8,642,356 B2
(45) Date of Patent: Feb. 4, 2014

(54) CASCADE ENZYME-LINKED IMMUNOSORBENT ASSAY

(75) Inventors: Sang Jeon Chung, Taejeon-si (KR); Young-mi Lee, Gumi-si (KR); Yu-Jin Jeong, Taejeon-si (KR); Hyo Jin Kang, Pohang-si (KR); Bong Hyun Chung, Taejeon-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 834 days.

(21) Appl. No.: 12/679,830

(22) PCT Filed: May 30, 2008

(86) PCT No.: PCT/KR2008/003067
§ 371 (c)(1),
(2), (4) Date: Mar. 24, 2010

(87) PCT Pub. No.: WO2009/044985
PCT Pub. Date: Apr. 9, 2009

(65) Prior Publication Data
US 2010/0196937 A1    Aug. 5, 2010

(30) Foreign Application Priority Data

Oct. 1, 2007    (KR) .......................... 10-2007-0098853

(51) Int. Cl.
*G01N 33/553*    (2006.01)
*G01N 33/573*    (2006.01)

(52) U.S. Cl.
USPC ............. 436/526; 435/24; 435/7.72; 435/7.9; 435/7.94

(58) Field of Classification Search
USPC .................... 435/24, 7.72, 7.9, 7.94; 436/526
See application file for complete search history.

(56) References Cited

U.S. PATENT DOCUMENTS

| 4,463,090 A | 7/1984 | Harris |
| 2002/0172953 A1* | 11/2002 | Mirkin et al. ................ 435/6 |

FOREIGN PATENT DOCUMENTS

| JP | 59-206762 | 11/1984 |
| JP | 02-275360 | 11/1990 |
| JP | 08-050024 | 2/1996 |
| JP | 11-075896 | 3/1999 |
| WO | 02-16634 | 2/2002 |
| WO | 2006-078289 | 7/2006 |
| WO | 2007-084192 | 7/2007 |

OTHER PUBLICATIONS

Brakeman, S. "DNA-Based Barcodes, Nanoparticles, and nanostructures for the Ultrasensitive Detection and Quantification of Proteins"; (2004) *Angew.Chem.Int.Ed.* 43:5730-5734.
Nam, J-M. et al. "Nanoparticle-Based Bio-Bar Codes for the Ultrasensitive Detection of Proteins"; (2003) *Science* 301:1884-1886.

(Continued)

*Primary Examiner* — Mark Shibuya
*Assistant Examiner* — Pensee Do
(74) *Attorney, Agent, or Firm* — Lathrop & Gage LLP

(57) ABSTRACT

The present invention relates to a cascade enzyme-linked immunosorbent assay, more precisely a cascade enzyme-linked immunosorbent assay using magnetic microparticles (MMPs) immobilized with the target antigen specific primary antibody and silica nanoparticles (SPs) immobilized with a cascade reaction initiator and the antigen-specific secondary antibody. When the method of the present invention is applied in the detection of an antigen in biosamples, the detection sensitivity can be significantly increased.

8 Claims, 6 Drawing Sheets

(56) References Cited

OTHER PUBLICATIONS

Niemeyer, C.M. et al. "Immuno-PCR: high sensitivity detection of proteins by nucleic acid amplification"; (2005) *Trends in Biotech.* 23(4); 208-216.

Sano, T. et al. "Immuno-PCR: Very Sensitive Antigen Detection by Means of Specific Antibody-DNA Conjugates"; (1992) *Science* 120-122.

Schweitzer, B. et al. "Immunoassays with rolling circle DNA amplification: A versatile platform for ultrasensitive antigen detection"; (2000) *PNAS* 97(18):10113-10119.

Yolken, R.H. et al. "Enzyme-Linked Fluorescence Assay: Ultrasensitive Solid-Phase Assay for Detection of Human Rotavirus"; (1979) *J. Clin.Microbiol.* 10(3):317-321.

Nam et al. (2003) "Nanparticle-Based Bio-Bar Codes for the Ultrasensitive Detection of Proteins," Science 301:1884-1886.

Bates D.L. (1987) "Enzyme Amplification in Diagnostics," Trends in Biotechnology 5:204-209.

McNeill et al. (2004) "A Simplified Cytokine Immunoassay Using Magnetic Polymer Particles," Scandinavian Journal Of Immunology 60:287-291.

* cited by examiner a)

Four Time Measuremet | Averaged Data b)

Four Time Measuremet | Averaged Data a)

b)

CASCADE ENZYME-LINKED IMMUNOSORBENT ASSAY

CROSS-REFERENCE TO RELATED APPLICATIONS

This application is the U.S. National Stage of International Application No. PCT/KR2008/003067, filed May 30, 2008 and published in English on Apr. 9, 2009 as WO 2009/044985, which claims the benefit of Korean Patent Application No. 10-2007-0098853, filed Oct. 1, 2007, both of which are hereby incorporated by reference to the extent not inconsistent with the disclosure herewith.

TECHNICAL FIELD

The present invention relates to a cascade enzyme-linked immunosorbent assay.

BACKGROUND ART

Immunoassay is a technique using an antibody for the analysis of a sample. In the early days of immunoassay, researchers mainly performed this technique to measure or detect a protein. But, recently with the advance of antibody-technique, immunoasaay has been widely performed to analyze low-molecular compounds, carbohydrates, lipids and many microorganisms. Among various immunoassays, the most preferred one is the sandwich enzyme-linked immunosorbent assay, which uses two different antibodies having different epitopes against one antigen. This method demonstrates high antigen selectivity, so that it has been largely used for diagnostic purpose.

To increase sensitivity in detection during immunoassay, methods for amplifying signals biochemically have been developed, for example IPCR (immuno-PCR) to amplify signals biochemically by using DNA and polymerase, Bio-barcode immunoassay to amplify signals chemically by using nanoparticles and DNA, cascade or proenzyme activation system to amplify signal biochemically (see FIG. 1, U.S. Pat. No. 4,463,090), etc. Regarding IPCR, it was reported that IPCR exhibited 100-10,000 times as high sensitivity as the typical immunoassay. However, this method has problems of poor reproducibility and quantitativeness. Besides, when polyclonal antibody is used, even the selectivity against antigen is decreased, suggesting that this method is not preferred for the application in biosamples (Brakmann S et al., *Angew Chem Int Ed* 43:5730-5734, 2004). Moreover, researchers continuously ask higher detection sensitivity (Yolken R H et al., *J. Clin. Microbiol.* 10:317-321, 1979).

Therefore, to increase detection sensitivity in enzyme-linked immunosorbent assay, the present inventors developed a novel cascade enzyme-linked immunoassay by linking a cascade reaction initiator to a nano-particle on which an antigen-specific antibody is immobilized.

DISCLOSURE

Technical Problem

It is an objective of the present invention to provide a method for detecting an antigen with improved detection sensitivity.

It is another objective of the present invention to provide a kit for antigen detection with improved detection sensitivity.

Technical Solution

To achieve the above objectives, the present invention provides a method for detecting an antigen comprising the following steps:

1) capturing a target antigen by using magnetic microparticles to which the target antigen-specific primary antibody is immobilized;

2) forming sandwich complexes by treating the captured antigen of step 1) with silica nanoparticles to which the antigen specific secondary antibody and cascade reaction initiator (cascading enzyme) are immobilized;

3) treating the sandwich complexes with a proenzyme to be converted as an active enzyme by the above cascade reaction initiator and a substrate for the active enzyme-specific signal formation; and, 4) measuring the variations of generated signals.

The present invention also provides a kit for detecting an antigen comprising magnetic microparticles to which the target antigen specific primary antibody is immobilized, silica nanoparticles to which a cascade reaction initiator and the target antigen-specific secondary antibody is immobilized, a proenzyme to be converted as an active enzyme by the cascade reaction initiator and a substrate for forming the active enzyme-specific signals.

Advantageous Effect

The method for detecting an antigen of the present invention provides significantly improved detection sensitivity to a target antigen in bio samples.

DESCRIPTION OF DRAWINGS

The application of the preferred embodiments of the present invention is best understood with reference to the accompanying drawings, wherein.

BEST MODE

Hereinafter, terms used in this invention are described.

"Cascade reaction" indicates a series of amplification reactions that one or more peptide bonds of an inactive proenzyme or zymogen are degraded by a cascade reaction activator so that the proenzyme or zymogen becomes an active enzyme and the activated enzyme decomposes a large amount of a specific substrate. By these two amplification steps, the signal detection capacity can be improved.

Hereinafter, the present invention is described in detail.

The present invention provides a method for detecting an antigen comprising the following steps:

1) capturing a target antigen by using magnetic microparticles (referred as MMPs hereinafter) to which the target antigen specific primary antibody is immobilized;

2) forming sandwich complex by treating the captured antigen of step 1) with silica nanoparticles (referred as SPs hereinafter) on which the antigen specific secondary antibody and cascade reaction initiator (cascading enzyme) are immobilized;

3) treating the sandwich complex with a proenzyme to be converted as an active enzyme by the above cascade reaction initiator and a substrate for the active enzyme-specific signal formation; and, 4) measuring the variations of generated signals.

Figure 1:
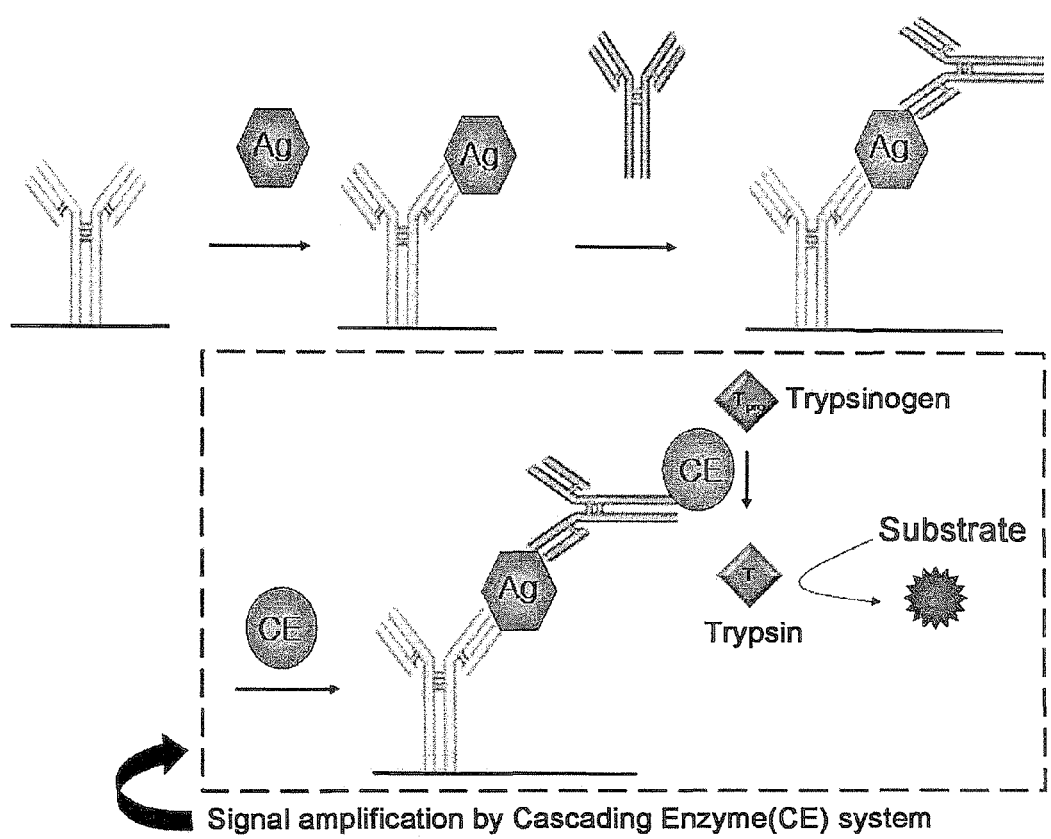
FIG. 1 is a diagram illustrating the amplification of antigen detection signals by cascade reaction.
Figure 2:
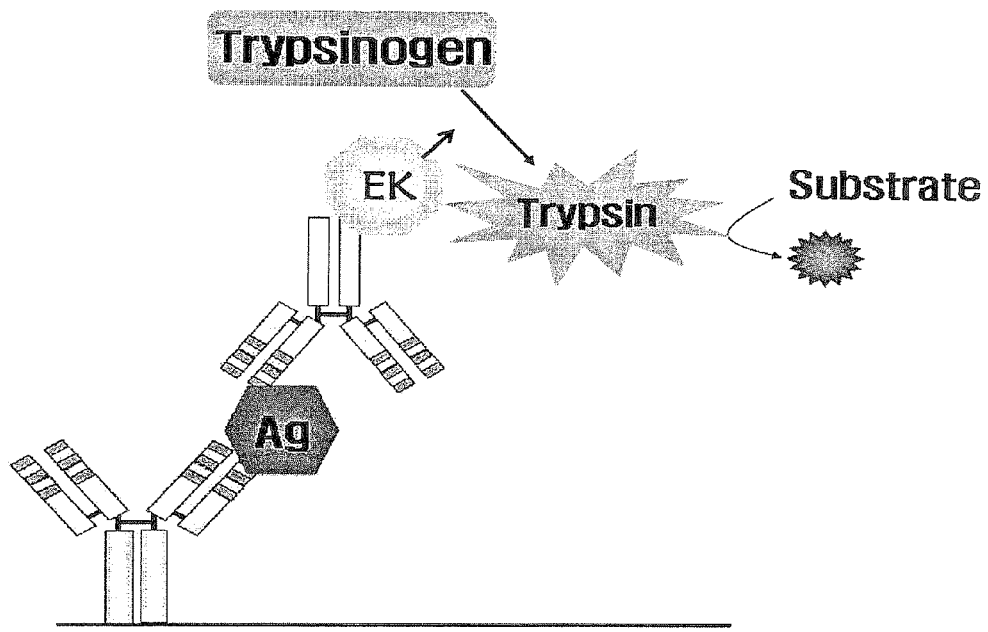
FIG. 2 is a diagram illustrating the amplification of antigen detection signals by PolyAb-EK of the present invention.
Figure 3:
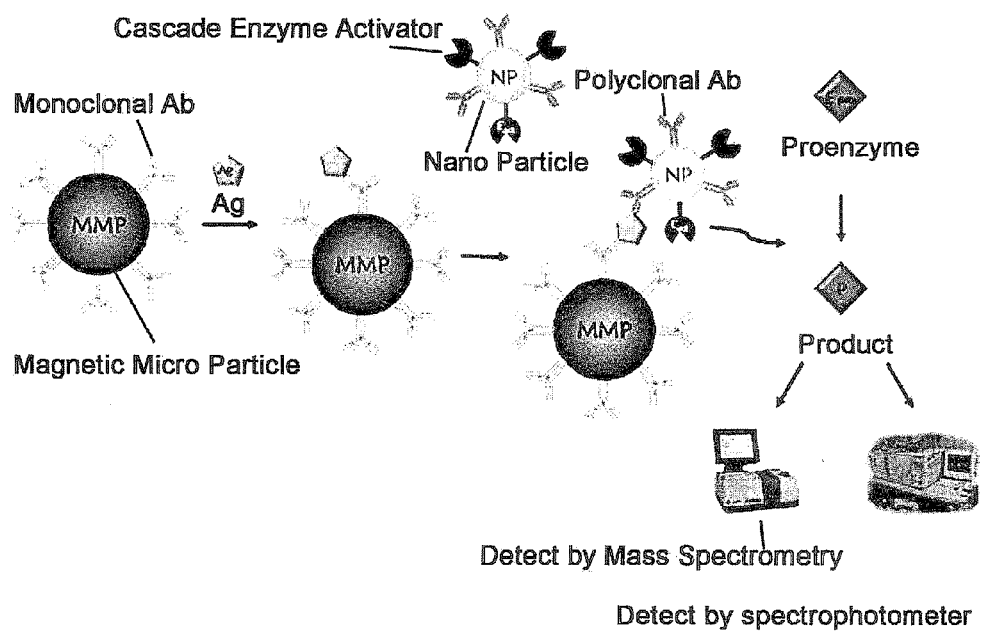
FIG. 3 is a diagram illustrating the amplification of antigen detection signals by PolyAb-Sp-EK of the present invention.

In a preferred embodiment of the present invention, AFP (alpha fetoprotein; hepatoma specific antigen) or PSA (prostate-specific antigen) was captured by using magnetic microparticles to which the AFP- or PSA-specific primary antibody was immobilized. Then, silica nanoparticles, to which the cascade reaction initiator, enterokinase and the antigen-specific antibody (polyAb-Sp-EK) were conjugated, were treated thereto. Trypsinogen, the proenzyme that would be converted into active trypsin by enterokinase and L-BApNA, the substrate for generating trypsin-specific signals, were treated thereto. Then, changes of the signals generated during the trypsin mediated L-BApNA reaction were measured (see FIGS. 3, 5 and 7). The control was prepared by linking enterokinase directly to the AFP- or PSA-specific secondary antibody (polyAb-EK) (see FIGS. 2, 5 and 6). As a result, when polyAb-EK was used, antibody detection was possible at the concentration of 50-100 pM, and when polyAb-Sp-EK was used, antibody detection was possible at the concentration of 1-10 pM. That is, when Sp was used, the effect of signal amplification increased at maximum 100 times the original. Therefore, it was confirmed that the silica nanoparticles of the present invention immobilized with the cascade reaction initiator, enterokinase and the antigen specific secondary antibody could be effectively used to increase antigen detection capacity.

For the proenzyme, any enzyme that can be converted into an active enzyme by the cascade reaction initiator is acceptable. Preferably, trypsinogen or chymotrypsinogen can be used, but not always limited thereto. For example, trypsinogen turns into active trypsin by using enterokinase as a cascade initiator, and chymotrypsinogen is converted into active chymotrypsin by using trypsin as a cascade initiator. Other examples of the cascade reaction are shown in Table 1.

TABLE 1

Examples of cascade reaction

| Cascade enzyme | Proenzyme | Active enzyme | Substrate |
|---|---|---|---|
| Enterokinase | Trypsinogen | Trypsin | N-alpha-benzyl-L-arginine pNALys-pNA |
| Trombinkinase | Prothrombin | Thrombin | Benzyloxycarbonyl-Gly-Pro-Arg-pNA |
| Trypsin | Chymotrypsinogen A, B | Chymotrypsin A, B | 7-glutarylphenylalnine-amino-4-methylcoumarin |
| Factor a | Prokallikrein | Kallikrein | Benzoyl-Pro-Phe-Arg-pNA |
| (active Hageman factor) | | | |
| Streptokinase plasmakinase Factor | Plasminogen | Plasmin | Benzyloxycarbonyl-Gly-Pro-Arg-pNACbz-Gly-Gly-Arg-(7-amino-4-methylcoumarin)amide |
| Dipeptidyl carboxypeptidase | Angiotensin I (partially active type) | Angiotensin II (entirely active type) | Hip-His-Leu, Hip-Gly-Gly[Hip; hippuric acid (benzoyl glycine)] |

Signals are generated when the active enzyme mediates the reaction of a substrate for signal generation, which can be presented by color development, radioactive ray, fluorescence, bioluminescence and chemiluminescence, etc. For the substrate for signal generation, any substrate that is specific to an active enzyme and is able to generate signals after the active enzyme mediated reaction can be used. The active enzyme, trypsin, is able to generate signals by using L-BApNA substrate (N-alpha-Benzoyl-L-arginine p-nitroanilide, hydrochloride) as the substrate for signal generation. In a preferred embodiment of the present invention, a colorimetric substrate or a fluorescent substrate was used as the substrate for the active enzyme converted from the proenzyme by a cascade reaction initiator and as a result, antigen was detected equally (see FIG. 4).

The methods for measuring the signals of step 4) are well known to those in the art. Briefly, if a substrate is an enzyme, the substrate reaction can be confirmed by measuring enzyme reaction; if a substrate is a fluorescent material, the substrate reaction can be confirmed by measuring fluorescent strength; and if a substrate is a radioactive substance, the substrate reaction can be confirmed by measuring the emission of radioactive rays, so that the antigen can be finally detected.

According to the method of the present invention, the step of eliminating remnants not reacted is included between each step by the conventional method well known to those in the art, but the present invention is not limited thereto.

Figure 8:
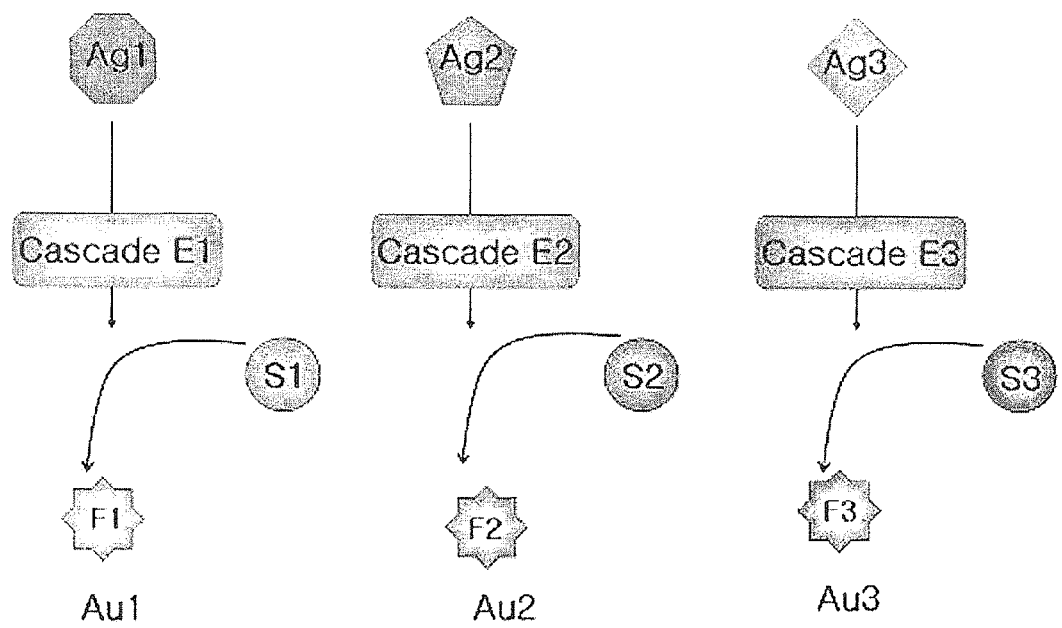
FIG. 8 is a diagram illustrating the multiplexed detection process capable of detecting different antigens at the same time.

In a preferred embodiment of the present invention, to detect a target antigen from a sample containing many different antigens, silica nanoparticles immobilized with the antigen specific secondary antibodies and different cascade reaction initiators were used (see FIG. 8).

The present invention also provides a kit for detecting an antigen comprising magnetic microparticles to which the target antigen specific primary antibody is immobilized, silica nanoparticles to which a cascade reaction initiator and the target antigen specific secondary antibody is immobilized, a proenzyme to be converted as an active enzyme by the cascade reaction initiator and a substrate for forming the active enzyme specific signals.

The kit can additionally include an antigen, washing solution, reaction buffer and blocking buffer.

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Monoclonal Antibody Immobilization

<1-1> Immobilization onto Magnetic Microparticles (MMPs) (monoAb-MMPs)

Tosyl-functionalized MMPs were conjugated with monoclonal PSA (prostate-specific antigen) antibody (Cat. No. MAB1344, R&D, USA) or monoclonal AFP (Alpha Fetoprotein) antibody (BodytechMed, Korea) by covalent bond using primary amino groups.

Particularly, 20 μl of MMPs (100 mg/ml; Invitrogen, USA) was washed three times with 0.2 M borate buffer (pH9.5), which was resuspended in 20 μl of borate buffer. 66 μl of 0.2 M borate buffer (pH 9.5), 84 μl of 3 M $(NH_4)_2SO_4$, 20 μl of MMPs and 80 μl of monoclonal PSA antibody solution or monoclonal AFP antibody solution (1.0 μg/μl dissolved in borate buffer) were all mixed to prepare binding solution. Binding reaction was induced at 37° C. with 220 rpm for 24 hours in a shaking incubator. As a result, generated monoAb-MMPs were recovered by using a magnetic and resuspended in 250 μl of blocking buffer (0.15M NaCl, 10 mM phosphate, 0.05% Tween-20, 1% BSA, pH 7.4), followed by passivation in a stirrer at 37° C. with 220 rpm for 24 hours. Then, the monoAb-MMPs were washed three times with 1 ml of blocking buffer, which were stored at 4° C. in 200 μl of blocking buffer (10 mg/ml).

<1-2> Immobilization onto Well Plate (monoAb-Well Plate)

Each well of the well plate containing oligoethyleneglycol activated by N-hydroxysuccinimide (NHS) on the surface (NUNC, England) was coated with 10 μg/ml of monoclonal PSA antibody or monoclonal AFP antibody. The well plate immobilized with the antibody was washed three times, followed by blocking with 300 μl of blocking buffer (0.25 M Ethanolamine, pH 8.5; Aldrich, USA).

10 μg/ml of monoclonal antibody (in 100 mM sodium phosphate buffer, pH 8.0) was added to the plate at the concentration of 100 μl/well, followed by slow agitation for one hour at room temperature for immobilization. After one hour of reaction, the plate was washed with PBS-T (1×PBS+0.05% Tween-20) three times.

Example 2

Polyclonal Antibody Immobilization

<2-1> Preparation of Polyclonal Antibody-Enterokinase Hybrid (polyAb-EK)

EK (11334115, Roche, Switzerland) was conjugated with polyclonal AFP antibody (BodytechMed, Korea) using sulfo-SMCC (sulfosuccinimidyl 4-[N-maleimidomethyl]cyclohexane-1-carboxylate; PIERCE, USA) to prepare the polyclonal antibody-EK hybrid.

First, 20 mM DTT was added to 500 μg of polyclonal PSA antibody (R&D, USA) or polyclonal AFP antibody, which stood at room temperature for 20 minutes, leading to the conversion of disulfide bond in Fc region of the antibody into SH group. Excessive DTT remaining after the reaction was eliminated by using PD-10 desalting column (GE). 50 equivalent of sulfo-SMCC (4.8 mg/ml in water) was added to 500 μg of EK and mixed at room temperature for 30 minutes to form EK-EMCC derivative. Excessive sulfo-SMCC remaining after the reaction was eliminated by using PD-10 desalting column (GE). The antibody inducing SH group and equivalent of EK-SMCC were mixed, followed by reaction at room temperature for one hour to prepare polyclonal antibody-EK hybrid. The prepared hybrid was purified by gel filtration and the conjugate was confirmed by Western blotting. At this time, 100 mM triethanolamine (pH 7.3, Sigma, USA) was used as reaction buffer.

<2-2> Preparation of Silica Nanoparticles (SPs) Immobilized with Polyclonal Antibody and EK (polyAb-SPs-EK)

SPs were conjugated with polyclonal PSA antibody and EK by amine coupling.

Particularly, 150 μl of 500 nm SPs (100 mg/ml; polysciences, USA) containing carboxylic acid on the surface was washed three times with TDW and resuspended in 150 μl of TDW. The SPs were mixed with 300 μl of the mixture of 0.4 M EDC [N-ethyl-N'-(dimethylaminopropyl) carbodiimide; Sigma-Aldrich, USA] and 0.1 M NHS (N-hydroxysuccinimide; Aldrich, USA) (1:1), followed by stirring at 25° C. for 30 minutes to activate carboxylic acid in SPs. Then, the mixture was washed with 0.1 M MES buffer (pH 6) twice and dispersed in 150 μl of MES buffer. 150 μl of SPs, 33.5 μl of polyclonal PSA antibody or polyclonal AFP antibody (0.83 μg/μl in PBS), 54 μl of EK (2.1 μg/μl in distilled water) and 262.5 μl of 0.1 M MES buffer were all mixed to prepare binding solution. The binding solution was stirred in a stirrer at 25° C. with 180 rpm for 2 hours to induce binding reaction. Centrifugation was performed at 830 g for 3 minutes. 0.25 M ethanolamine (pH 8.5; Aldrich, USA) was added thereto, followed by reaction at 25° C. for 30 minutes to inactivate the remaining active residues (NHS ester). Then, blocking buffer (0.1 M borate buffer, 1% BSA, 0.05% Tween-20, pH 8.5) was added thereto, followed by reaction at 25° C. for 30 minutes. The reaction mixture was washed with blocking buffer twice and then mixed with 1.5 ml of blocking buffer, which was stored at 4° C.

Experimental Example 1

Detection of an Antigen (AFP) Using polyAb-EK

<1-1> Capturing of an Antigen by Using monoAb-Well Plate and polyAb-EK

AFP antigen solution (Biodesign, USA) was added to monoAb-well plate washed with assay buffer (50 mM Tris, 150 mM NaCl, 0.1% BSA, 0.2% tween-20, pH 7.4) three times, followed by reaction at 25° C. for 1 hour. Concentrations of AFP were 10 nM, 1 nM, 100 pM, 10 pM, 1 pM, 100 fM, 10 fM and 1 aM, and the control was not treated with AFP. The well plate was washed with assay buffer 5 times, to which polyAb-EK:AFP was added. The mixture was incubated at 25° C. for 1 hour. Then, the mixture was washed with assay buffer three times and enzyme activity was measured.

<1-2> Signal Generation and Detection

The hybrid obtained in Experimental Example <1-1> mediated by the antigen and trypsinogen (Sigma, USA) were mixed in 10 μM tris buffer (pH 8.0). The mixture was reacted at 37° C. for 2 hours. Then, 1 mM L-BApNa substrate (colorimetric substrate; N-alpha-Benzoyl-L-arginine p-Nitroanilide, hydrochloride; MPBIO, USA) was added and $OD_{410}$ was measured. N-alpha-Benzoyl-L-arginine 7-amido-4-methylcoumarin HCL substrate (fluorescent substrate; Sigma, USA) was added and fluorescence was measured at Ex 333 nm/Em 440 nm.

Figure 4:
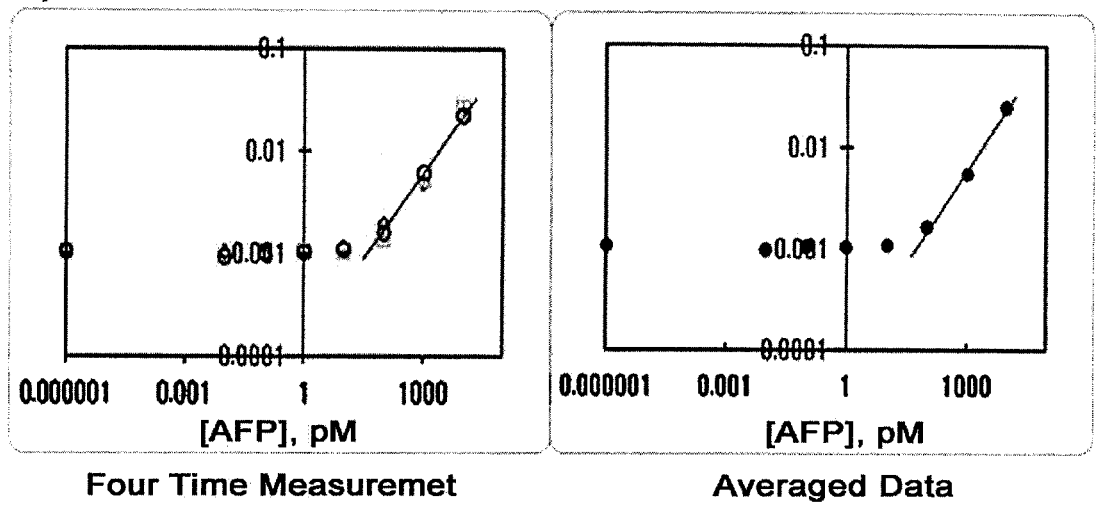
FIG. 4 is a set of graphs illustrating the amplification of antigen detection signals by PolyAb-EK of the present invention using colorimetric substrate or fluorescent substrate:
 a: colorimetric substrate; and,
 b: fluorescent substrate.
Figure 4:
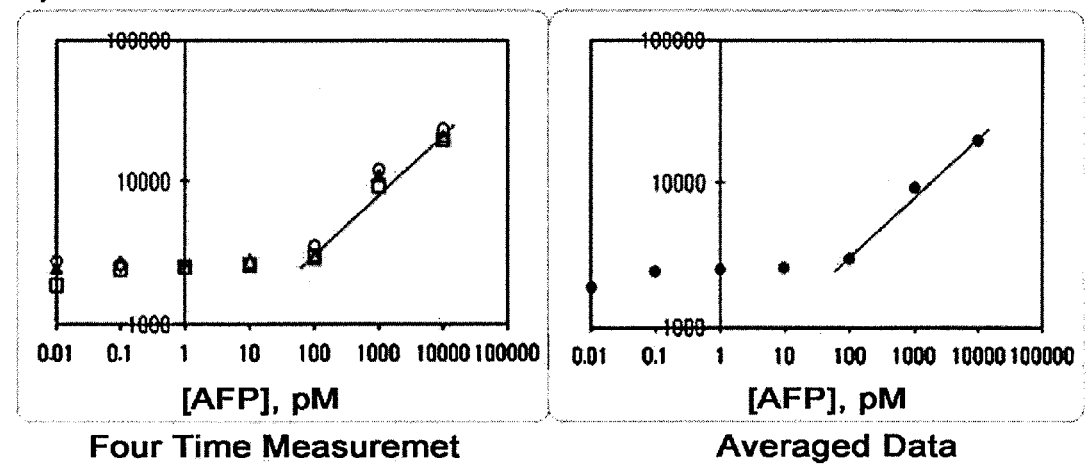

As a result, as shown in FIG. 4, high reproducibility was confirmed in antigen detection and antigen detection results were consistent when colorimetric substrate and fluorescent substrate were used respectively.

Experimental Example 2

Detection of an Antigen (AFP) Using polyAb-EK or polyAb-Sp-EK

<2-1> Capturing of an Antigen by Using monoAb-Well Plate and polyAb-EK

An experiment was performed by the same manner as described in Experimental Example 1-1 except that the concentrations of AFP were 100 nM, 10 nM, 1 nM, 100 pM and 1 pM.

<2-2> Capturing of an Antigen by Using monoAb-MMPs and polyAb-Sp-EK

AFP antigen solution was added to monoAb-MMPs (10 mg/ml) washed with assay buffer twice, followed by reaction at 25° C. for 2 hours. The concentrations of AFP antigen were 100 nM, 10 nM, 1 nM and 100 pM. Upon completion of the reaction, the monoAb-MMPs and AFP conjugate was washed with assay buffer once and then loaded in blocking buffer (50 mM Tris, 150 mM NaCl, 1% BSA, 0.2% tween-20, pH 7.4), followed by reaction at 25° C. for 30 minutes. Then, the mixture was washed with assay buffer twice, to which polyAb-SPs-EK (10 mg/ml) was added, followed by reaction at 25° C. for 2 hours. The mixture was washed with assay buffer 5 times and then enzyme activity was measured.

<2-3> Signal Generation and Detection

The hybrid obtained in Experimental Example <2-1> or <2-2> mediated by the antigen and trypsinogen (the control was not treated with trypsinogen) were mixed in 10 μM tris buffer (pH 8.0), followed by reaction at 37° C. for 20 hours. Upon completion of the reaction, 1 mM L-BApNA substrate was added and $OD_{410}$ was measured.

Figure 5:
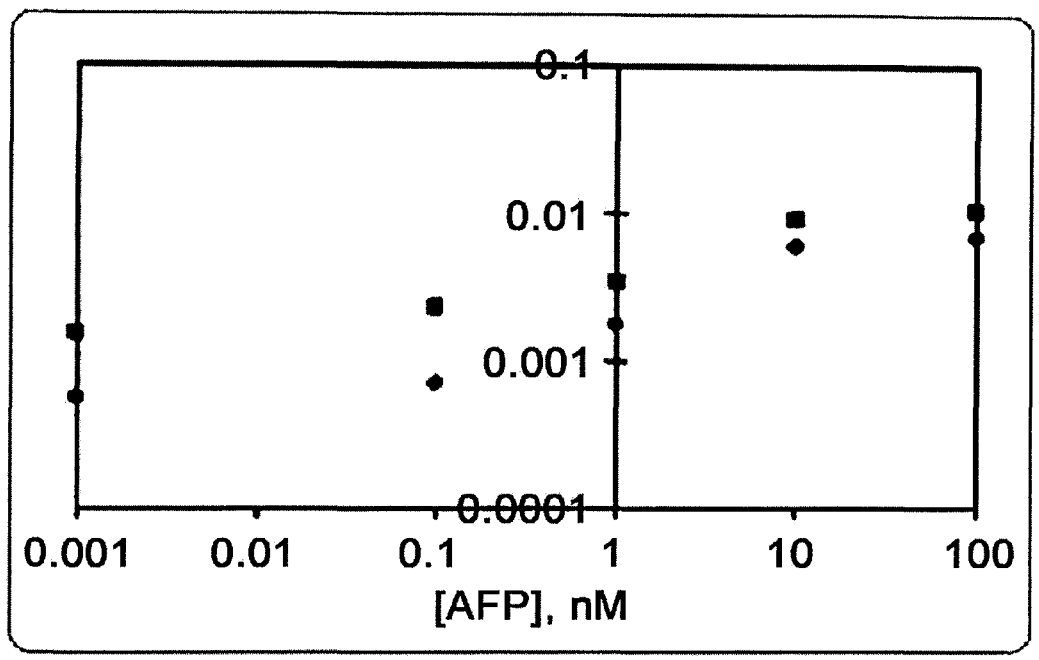
FIG. 5 is a set of graphs illustrating the amplification of antigen detection signals by PolyAb-EK:AFP or PolyAb-Sp-EK:AFP of the present invention:
 a: PolyAb-EK; and,
 b: PolyAb-Sp-EK.
Figure 5:
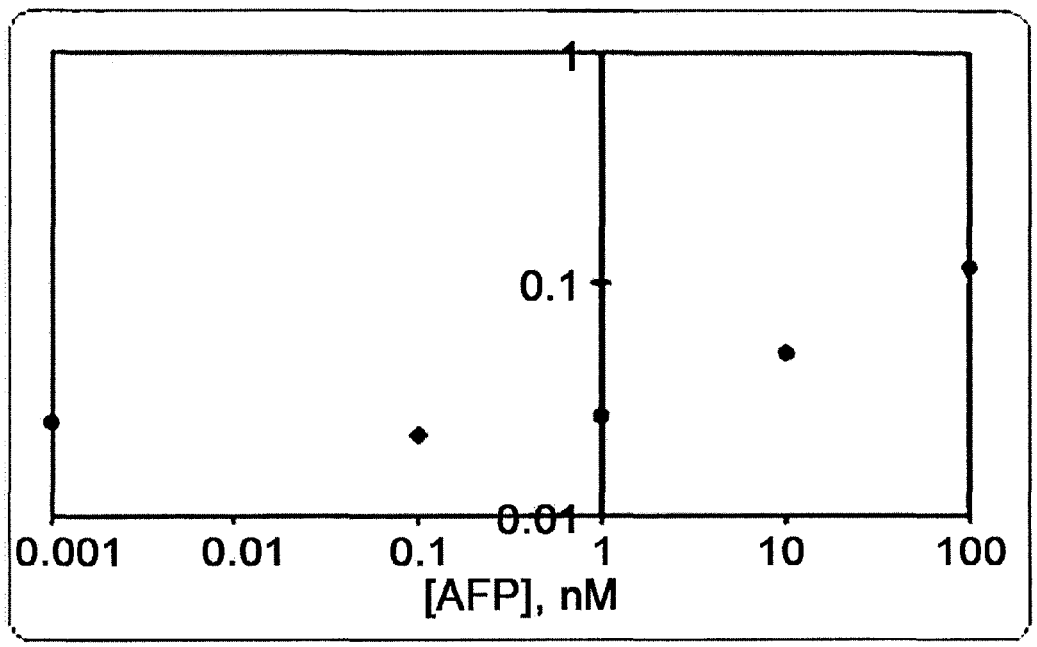

As a result, as shown in FIG. 5, the target antigen was detected at polyAb-EK concentration of 100 pM and at polyAb-Sp-EK concentration of 1-10 pM. That is, when Sp was used, amplification of signal for detection was at least 100 times higher. When MMPs were used, however, reproducibility was lower after repeated experiments.

Experimental Example 3

Detection of an Antigen (PSA) Using polyAb-EK or polyAb-Sp-EK

<3-1> Capturing of an Antigen by Using monoAb-Well Plate and polyAb-EK

An experiment to capture the antigen was performed by the same manner as described in Experimental Example <1-1> except that PSA antigen (Sigma-Aldrich, USA) was used instead of ASP antigen and the concentrations of PSA were 5 nM, 1 nM, 500 pM, 100 pM, 50 pM, 10 pM and 1 pM.

<3-2> Capturing of an Antigen by Using monoAb-MMPs and polyAb-Sp-EK

An experiment to capture the antigen was performed by the same manner as described in Experimental Example <2-2> except that PSA antigen was used instead of ASP antigen and the concentrations of PSA were 10 nM, 1 nM, 100 pM, 10 pM and 1 pM.

<3-3> Signal Generation and Detection

The hybrid obtained in Experimental Example <3-1> or <3-2> mediated by the antigen and trypsinogen (the control was not treated with trypsinogen) were mixed in 10 μM tris buffer (pH 8.0), followed by reaction at 37° C. for 20 hours. Upon completion of the reaction, 1 mM L-BApNA substrate was added and $OD_{410}$ was measured.

Figure 6:
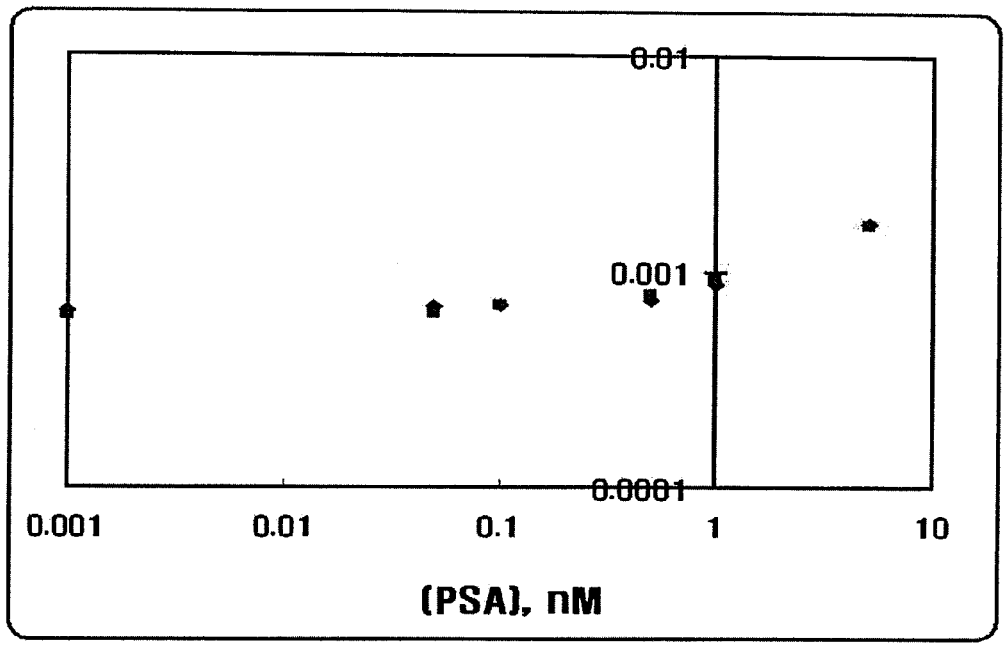
FIG. 6 and FIG. 7 are graphs illustrating the amplification of antigen detection signals by PolyAb-EK:PSA and PolyAb-Sp-EK:PSA of the invention respectively.
Figure 7:
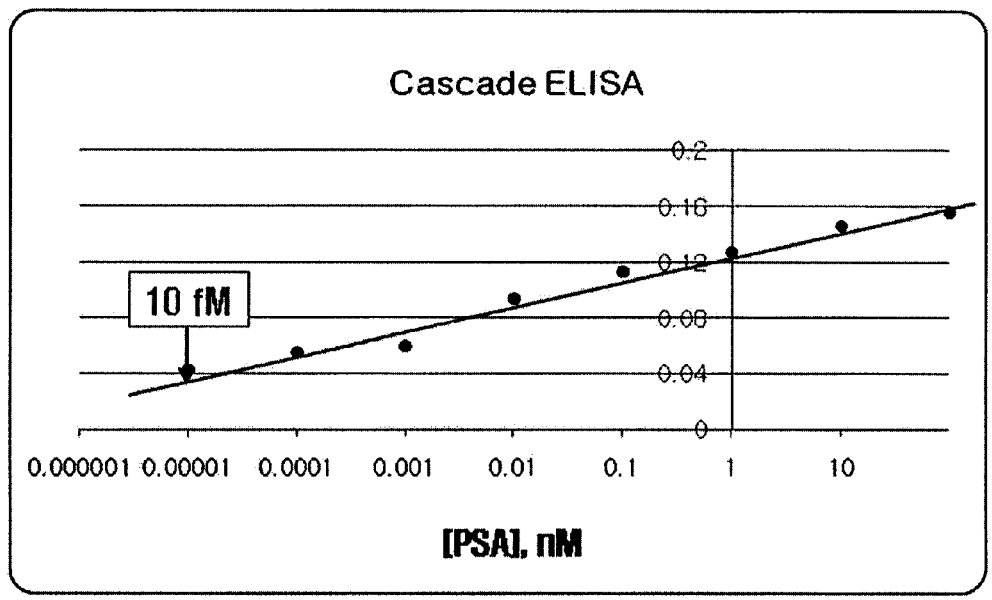

As a result, as shown in FIG. 6 and FIG. 7, the antigen could be detected at polyAb-Ek concentration of 50 pM and at polyAb-Sp-EK concentration of 1-10 pM. That is, when Sp was used, amplification of signal for detection was 100 times higher at maximum and reproducibility was also very high after repeated experiment using the well plate.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A method for detecting a target antigen comprising the following steps:
    1) capturing the target antigen by using magnetic microparticles or well plates to which a target antigen-specific primary antibody is immobilized;
    2) forming sandwich complexes by treating the captured antigen of step 1) with silica nanoparticles to which an antigen specific secondary antibody and cascade reaction initiator (cascading enzyme) are immobilized;
    3) treating the sandwich complexes with a proenzyme to be converted as an active enzyme by the cascade reaction initiator and a substrate for active enzyme-specific signal formation thereby generating signals; and,
    4) measuring the variations of generated signals, wherein detection of an increase or decrease in the generated signals indicates the presence of the target antigen.

2. The method according to claim 1, wherein the proenzyme is trypsinogen or chymotrypsinogen.

3. The method according to claim 2, wherein the trypsinogen is activated and changed into trypsin by using enterokinase as a cascade reaction initiator.

4. The method according to claim 2, wherein the chymotrypsinogen is activated and changed into chymotrypsin by using trypsin as a cascade reaction initiator.

5. The method according to claim 3, wherein the trypsin generates signals by using L-BApNA (N-alpha-Benzoyl-L-arginine p-Nitroanilide, hydrochloride) or N-alpha-benzoyl-L-arginine 7-amido-4-methyl-coumarin HCL as a substrate for signal formation.

6. The method according to claim 1, wherein the signal formed is presented by one or more methods selected from the group consisting of color development, fluorescence, bioluminescence and chemiluminescence.

7. A kit for detecting a target antigen comprising magnetic microparticles or well plates to which a target antigen specific primary antibody is immobilized, silica nanoparticles to which a cascade reaction initiator and a target antigen specific secondary antibody are immobilized, a proenzyme to be converted as an active enzyme by the cascade reaction initiator and a substrate for forming active enzyme specific signals.

8. The kit according to claim 7, wherein the kit additionally includes an antigen, washing solution, reaction buffer and blocking buffer.

* * * * *